US008929986B2

(12) United States Patent
Parker et al.

(10) Patent No.: US 8,929,986 B2
(45) Date of Patent: Jan. 6, 2015

(54) MEDICAL DEVICE COMMUNICATION AND CHARGING ASSEMBLIES FOR USE WITH IMPLANTABLE SIGNAL GENERATORS, AND ASSOCIATED SYSTEMS AND METHODS

(71) Applicant: Nevro Corporation, Menlo Park, CA (US)

(72) Inventors: Jon Parker, San Jose, CA (US); Yougandh Chitre, Santa Clara, CA (US); Andre B. Walker, Monte Sereno, CA (US)

(73) Assignee: Nevro Corporation, Menlo Park, CA (US)

( * ) Notice: Subject to any disclaimer, the term of this patent is extended or adjusted under 35 U.S.C. 154(b) by 0 days.

(21) Appl. No.: 13/669,350

(22) Filed: Nov. 5, 2012

(65) Prior Publication Data

US 2013/0116763 A1 May 9, 2013

Related U.S. Application Data

(60) Provisional application No. 61/556,097, filed on Nov. 4, 2011.

(51) Int. Cl.
| *A61N 1/375* | (2006.01) |
| *A61N 1/36* | (2006.01) |
| *H01R 43/16* | (2006.01) |
| *A61N 1/378* | (2006.01) |
| *A61N 1/372* | (2006.01) |
| *H01F 38/14* | (2006.01) |

(52) U.S. Cl.
CPC ............ *A61N 1/36071* (2013.01); *H01R 43/16* (2013.01); *A61N 1/375* (2013.01); *A61N 1/3787* (2013.01); *A61N 1/37229* (2013.01); *H01F 38/14* (2013.01)
USPC .......................................................... 607/36

(58) Field of Classification Search
USPC ................. 607/36, 46, 60, 117, 156; 343/728
See application file for complete search history.

(56) References Cited

U.S. PATENT DOCUMENTS

| D250,719 S | 1/1979 | Jacobson et al. |
| 4,441,498 A | 4/1984 | Nordling |
| D280,930 S | 10/1985 | Speicher et al. |

(Continued)

FOREIGN PATENT DOCUMENTS

RU 2286182 C2 10/2006

OTHER PUBLICATIONS

International Search Report and Written Opinion for International Patent Application No. PCT/US2012/063617, Applicant: Nevro Corporation, mailed Feb. 28, 2013, 7 pages.
U.S. Appl. No. 13/607,617, filed Sep. 7, 2012, Thacker et al.

(Continued)

*Primary Examiner* — Carl H Layno
*Assistant Examiner* — Erica Lee
(74) *Attorney, Agent, or Firm* — Perkins Coie LLP

(57) ABSTRACT

Communication and charging assemblies for medical devices are disclosed herein. A communication and charging assembly in accordance with a particular embodiment includes a support element, with a communication antenna and a charging coil coupled to the support element. The charging coil can include wire loops having a plurality of wires and the support element can include a mounting surface shaped to match the charging coil and the communication antenna. In one embodiment, the communication and charging assembly are mounted in a header of an implantable signal generator.

14 Claims, 10 Drawing Sheets

(56) References Cited

U.S. PATENT DOCUMENTS

| | | | |
|---|---|---|---|
| 5,144,946 A | 9/1992 | Weinberg et al. | |
| D337,820 S | 7/1993 | Hooper et al. | |
| D343,901 S | 2/1994 | Anderson | |
| 5,769,877 A | 6/1998 | Barreras, Sr. | |
| 5,928,272 A | 7/1999 | Adkins et al. | |
| 5,954,758 A | 9/1999 | Peckham et al. | |
| 6,026,328 A | 2/2000 | Peckham et al. | |
| 6,208,902 B1 | 3/2001 | Bojeva et al. | |
| 6,453,198 B1 | 9/2002 | Torgerson et al. | |
| 6,505,072 B1 * | 1/2003 | Linder et al. | 607/32 |
| 6,553,263 B1 | 4/2003 | Meadows et al. | |
| D478,990 S | 8/2003 | Kroll | |
| 6,662,052 B1 | 12/2003 | Sarwal et al. | |
| 6,941,171 B2 | 9/2005 | Mann et al. | |
| D523,144 S | 6/2006 | Wenger et al. | |
| 7,062,330 B1 | 6/2006 | Boveja et al. | |
| 7,167,756 B1 | 1/2007 | Torgerson et al. | |
| 7,177,703 B2 | 2/2007 | Boveja et al. | |
| 7,184,836 B1 | 2/2007 | Meadows et al. | |
| 7,209,792 B1 | 4/2007 | Parramon et al. | |
| 7,239,918 B2 | 7/2007 | Strother et al. | |
| 7,254,449 B2 | 8/2007 | Karunasiri | |
| D559,987 S | 1/2008 | Strother et al. | |
| 7,328,068 B2 | 2/2008 | Spinelli et al. | |
| 7,330,762 B2 | 2/2008 | Boveja et al. | |
| 7,363,087 B2 | 4/2008 | Nghiem et al. | |
| 7,427,280 B2 | 9/2008 | Gerber | |
| 7,444,184 B2 | 10/2008 | Boveja et al. | |
| 7,493,159 B2 | 2/2009 | Hrdlicka et al. | |
| 7,496,404 B2 | 2/2009 | Meadows et al. | |
| 7,554,493 B1 | 6/2009 | Rahman | |
| 7,561,919 B2 | 7/2009 | Shalev et al. | |
| 7,620,454 B2 | 11/2009 | Dinsmoor et al. | |
| 7,636,602 B2 | 12/2009 | Baru Fassio et al. | |
| D610,261 S | 2/2010 | Strother et al. | |
| 7,702,387 B2 | 4/2010 | Stevenson et al. | |
| 7,729,758 B2 | 6/2010 | Haller et al. | |
| 7,769,442 B2 | 8/2010 | Shafer | |
| 7,769,462 B2 | 8/2010 | Meadows et al. | |
| 7,801,615 B2 | 9/2010 | Meadows et al. | |
| 7,813,809 B2 | 10/2010 | Strother et al. | |
| 7,818,068 B2 | 10/2010 | Meadows et al. | |
| 7,865,245 B2 | 1/2011 | Torgerson et al. | |
| 7,916,013 B2 | 3/2011 | Stevenson | |
| 8,170,675 B2 | 5/2012 | Alataris et al. | |
| D663,035 S | 7/2012 | Smith | |
| D665,086 S | 8/2012 | Smith | |
| D665,087 S | 8/2012 | Smith | |
| 8,260,432 B2 | 9/2012 | DiGiore et al. | |
| 2003/0114899 A1 | 6/2003 | Woods et al. | |
| 2003/0191504 A1 | 10/2003 | Meadows et al. | |
| 2003/0195581 A1 | 10/2003 | Meadows et al. | |
| 2003/0204222 A1 | 10/2003 | Leinders et al. | |
| 2005/0049655 A1 | 3/2005 | Boveja et al. | |
| 2005/0131467 A1 | 6/2005 | Boveja | |
| 2005/0131486 A1 | 6/2005 | Boveja et al. | |
| 2005/0131487 A1 | 6/2005 | Boveja et al. | |
| 2005/0137644 A1 | 6/2005 | Boveja et al. | |
| 2005/0143787 A1 | 6/2005 | Boveja et al. | |
| 2005/0149146 A1 | 7/2005 | Boveja et al. | |
| 2005/0154425 A1 | 7/2005 | Boveja et al. | |
| 2005/0154426 A1 | 7/2005 | Boveja et al. | |
| 2005/0165458 A1 | 7/2005 | Boveja et al. | |
| 2005/0187590 A1 | 8/2005 | Boveja et al. | |
| 2005/0197678 A1 | 9/2005 | Boveja et al. | |
| 2005/0216070 A1 | 9/2005 | Boveja et al. | |
| 2006/0247684 A1 | 11/2006 | Halperin et al. | |
| 2007/0060955 A1 | 3/2007 | Strother et al. | |
| 2007/0060968 A1 | 3/2007 | Strother et al. | |
| 2007/0060979 A1 | 3/2007 | Strother et al. | |
| 2007/0060980 A1 | 3/2007 | Strother et al. | |
| 2007/0067000 A1 | 3/2007 | Strother et al. | |
| 2007/0067004 A1 | 3/2007 | Boveja et al. | |
| 2007/0073357 A1 | 3/2007 | Rooney et al. | |
| 2007/0119741 A1 | 5/2007 | Wenger et al. | |
| 2007/0123947 A1 | 5/2007 | Wenger et al. | |
| 2008/0039904 A1 | 2/2008 | Bulkes et al. | |
| 2008/0049376 A1 | 2/2008 | Stevenson et al. | |
| 2008/0077184 A1 | 3/2008 | Denker et al. | |
| 2009/0157155 A1 | 6/2009 | Bradley | |
| 2009/0204173 A1 | 8/2009 | Fang et al. | |
| 2009/0280153 A1 | 11/2009 | Hunter et al. | |
| 2009/0306491 A1 | 12/2009 | Haggers | |
| 2010/0023069 A1 | 1/2010 | Moffitt et al. | |
| 2010/0023097 A1 | 1/2010 | Peterson et al. | |
| 2010/0137938 A1 | 6/2010 | Kishawi et al. | |
| 2010/0137943 A1 | 6/2010 | Zhu | |
| 2010/0137944 A1 | 6/2010 | Zhu | |
| 2010/0168818 A1 * | 7/2010 | Barror et al. | 607/60 |
| 2010/0198298 A1 | 8/2010 | Glukhovsky et al. | |
| 2010/0198312 A1 | 8/2010 | Stevenson et al. | |
| 2010/0222844 A1 | 9/2010 | Troosters et al. | |
| 2010/0222856 A1 | 9/2010 | Halperin et al. | |
| 2010/0222857 A1 | 9/2010 | Halperin et al. | |
| 2010/0241195 A1 | 9/2010 | Meadows et al. | |
| 2010/0274314 A1 | 10/2010 | Alataris et al. | |
| 2010/0331920 A1 | 12/2010 | DiGiore et al. | |
| 2010/0331926 A1 | 12/2010 | Lee et al. | |
| 2011/0054551 A1 | 3/2011 | Zhu et al. | |
| 2011/0112601 A1 * | 5/2011 | Meadows et al. | 607/42 |
| 2011/0144468 A1 | 6/2011 | Boggs et al. | |
| 2011/0166621 A1 | 7/2011 | Cowan et al. | |
| 2013/0066399 A1 * | 3/2013 | Min | 607/59 |

OTHER PUBLICATIONS

U.S. Appl. No. 29/436,395, filed Nov. 5, 2012, Parker.
U.S. Appl. No. 29/451,693, filed Apr. 5, 2013, Parker.
Ostrovsky, Gene, "The Tantalus II System," MedGadget, http://www.medgadget.com/2007/12/the_tantalus_ii_system.html, Dec. 11, 2007, 3 pages.
Ptrutchi et al., Tantalus II System for Treating Metabolic Syndrome, http://www.implantable-device.com/2011/12/13/tantalus-ii-system-for-treating-metabolic-syndrome Dec. 13, 2011, 10 pages.

* cited by examiner

MEDICAL DEVICE COMMUNICATION AND CHARGING ASSEMBLIES FOR USE WITH IMPLANTABLE SIGNAL GENERATORS, AND ASSOCIATED SYSTEMS AND METHODS

CROSS-REFERENCE TO RELATED APPLICATION(S)

The present application claims priority to U.S. Provisional Application 61/556,097, filed Nov. 4, 2011, and titled MEDICAL DEVICE COMMUNICATION AND CHARGING ASSEMBLIES FOR USE WITH IMPLANTABLE PULSE GENERATORS, AND ASSOCIATED SYSTEMS AND METHODS, the entirety of which is incorporated by reference herein. To the extent the foregoing application and/or any other materials incorporated herein by reference conflict with the present disclosure, the present disclosure controls.

TECHNICAL FIELD

The present technology is directed generally to communication and charging assemblies for medical devices, and associated systems and methods. Communication antennas in accordance with the present technology are suitable for transmitting and receiving communications between medical device components, including communications between an implantable signal generator of a neurological stimulation system and external medical devices. Charging coils in accordance with the present technology are suitable for charging medical devices, including implantable signal generators.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator (sometimes referred to as an "implantable pulse generator" or "IPG") that is operably coupled to one or more leads that deliver electrical signals or pulses to neurological tissue or muscle tissue. For example, several neurological stimulation systems for spinal cord stimulation (SCS) have cylindrical leads that include a lead body with a circular cross-sectional shape and multiple conductive rings spaced apart from each other at the distal end of the lead body. The conductive rings operate as individual electrodes or contacts to deliver electrical signals to the patient. The SCS leads are typically implanted either surgically or percutaneously through a needle inserted into the epidural space, often with the assistance of a stylet.

Once implanted, the signal generator applies electrical signals to the electrodes, which in turn modify the function of the patient's nervous system, such as by altering the patient's responsiveness to sensory stimuli and/or altering the patient's motor-circuit output. In particular, the electrical signals can generate sensations that mask or otherwise alter the patient's sensation of pain. For example, in many cases, patients report a tingling or paresthesia that is perceived as more pleasant and/or less uncomfortable than the underlying pain sensation. In other cases, the patients can report pain relief without paresthesia or other sensations. As used herein, unless explicitly stated otherwise, the terms "pulses" and "signals" are used interchangeably to include any waveform shapes, whether continuous or discontinuous, including but not limited to sinusoidal or non-sinusoidal waves such as square waves, triangle waves, sawtooth waves, etc.

The implantable signal generator generally includes a communication antenna that allows operational parameters of the stimulation system to be altered, without necessitating a hard wired external connection. Implantable signal generators often include a charging coil that allows a battery in the implantable signal generator to be recharged from an external power source. The design of the communication antenna and the charging coil, and their locations within the implantable signal generator, can significantly impact the performance of the stimulation system. If the antenna and/or the coil are poorly positioned or shielded, updating operational parameters and/or charging the implantable signal generator can be difficult or impossible. For example, in many existing systems it can be difficult for a patient or an operator to correctly position an external device to transmit signals to the implantable signal generator. Additionally, poor coil design or shielding interference can decrease the efficiency of the charging process and cause increased heating. Prior systems suffer from many of these and/or additional drawbacks.

DETAILED DESCRIPTION

The present technology is directed generally to communication and charging assemblies for medical devices, and more specifically to communication and charging assemblies for implantable neurological modulation systems. At least some embodiments of the present technology include implantable signal generators having communication antennas and/or charging coils in a header of the signal generator. The communication antennas can be constructed, shaped and positioned in various manners to provide improved, enhanced, more robust and/or more effective signal reception and/or generation. The charging coils can be constructed, shaped and positioned to enhance charging efficiency and decrease heat generation. In other embodiments, the devices, systems and associated methods can have different configurations, components, and/or procedures. Still other embodiments may eliminate particular components and/or procedures. The present technology, which includes associated devices, systems, and procedures, may include other embodiments with additional elements or steps, and/or may include other embodiments without several of the features or steps shown and described below with reference to FIGS. 1-12. Several aspects of overall systems configured in accordance with the disclosed technology are described with reference to FIG. 1, and features specific to particular communication and charging assemblies are then discussed with reference to FIGS. 2-12.

Figure 1:
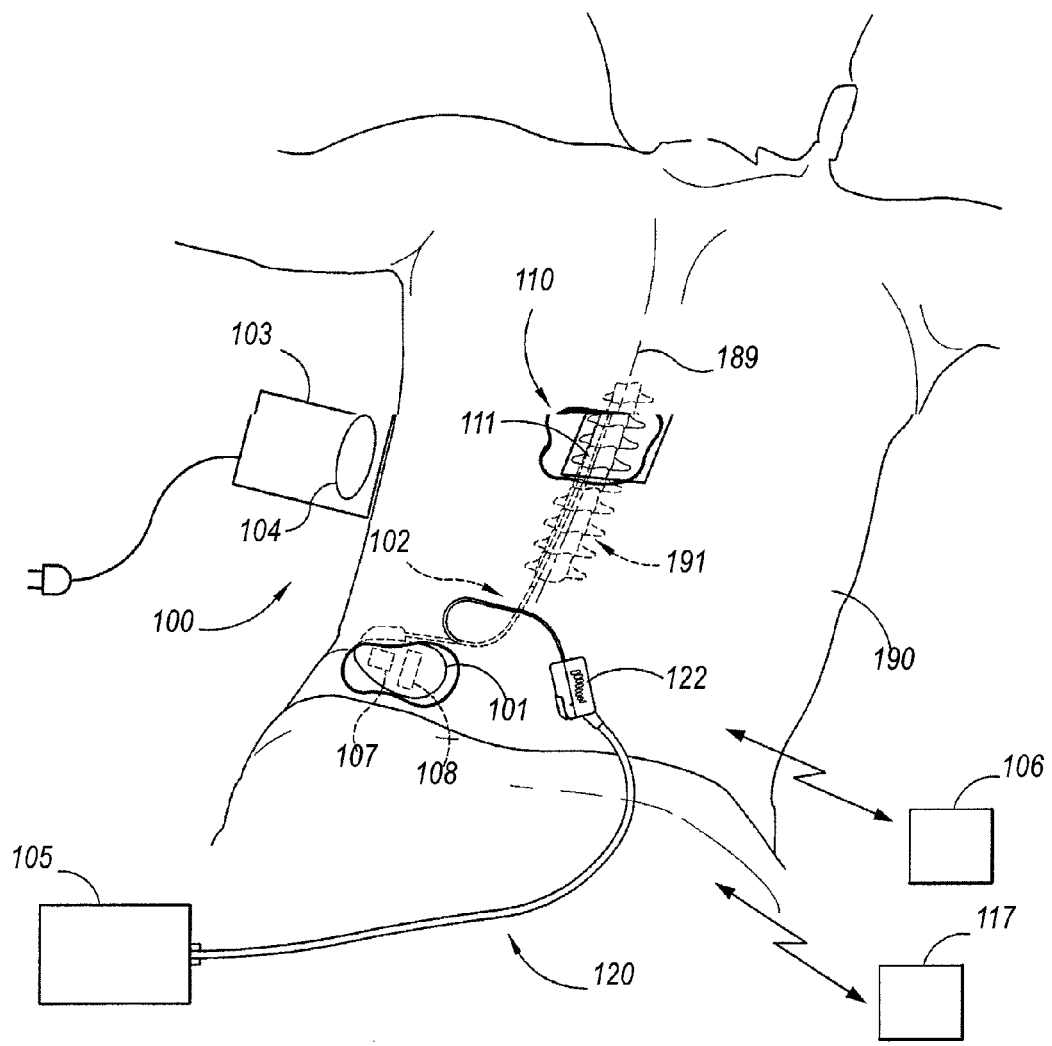
FIG. 1 is a partially schematic illustration of an implantable spinal cord modulation system positioned at a patient's spine to deliver therapeutic signals in accordance with an embodiment of the present technology.

FIG. 1 schematically illustrates a representative patient system 100 for providing relief from chronic pain and/or other conditions, arranged relative to the general anatomy of a patient's spinal cord 191. The overall patient system 100 can include a signal delivery device 110, which may be implanted within a patient 190, typically at or near the patient's spinal cord midline 189, and coupled to a signal generator 101 (e.g., a pulse generator). The signal delivery device 110 carries features for delivering therapy to the patient 190 after implantation. The signal generator 101 can be connected directly to the signal delivery device 110, or it can be coupled to the signal delivery device 110 via a signal link or lead extension 102. In a further representative embodiment, the signal delivery device 110 can include one or more elongated lead(s) or lead body or bodies 111. As used herein, the terms "lead" and "lead body" include any of a number of suitable substrates and/or support members that carry devices for providing therapy signals to the patient 190. For example, the lead or leads 111 can include one or more electrodes or electrical contacts that direct electrical signals into the patient's tissue, such as to provide for patient pain relief. In other embodiments, the signal delivery device 110 can include structures other than a lead body (e.g., a paddle) that also direct electrical signals and/or other types of signals to the patient 190.

The signal generator 101 can transmit signals (e.g., electrical signals or therapy signals) to the signal delivery device 110 that up-regulate (e.g., stimulate or excite) and/or down-regulate (e.g., block or suppress) target nerves. As used herein, and unless otherwise noted, to "modulate" or provide "modulation" to the target nerves refers generally to having either type of the foregoing effects on the target nerves. The signal generator 101 can include a machine-readable (e.g., computer-readable) medium containing instructions for generating and transmitting suitable therapy signals. The signal generator 101 and/or other elements of the system 100 can include one or more processor(s) 107, memory unit(s) 108 and/or input/output device(s) (not shown). Accordingly, the process of providing therapy signals, providing guidance information for positioning the signal delivery device(s) 110, and/or executing other associated functions can be performed by computer-executable instructions contained by computer-readable media located at the signal generator 101 and/or other system components. The signal generator 101 can include multiple portions, elements, and/or subsystems (e.g., for directing signals in accordance with multiple signal delivery parameters), carried in a single housing, as shown in FIG. 1, or in multiple housings.

In some embodiments, the signal generator 101 can obtain power to generate the therapy signals from an external power source 103. The external power source 103 can transmit power to the implanted signal generator 101 using electromagnetic induction (e.g., RF signals). For example, the external power source 103 can include an external coil 104 that communicates with a corresponding internal coil (not shown) within the implantable pulse generator 101. The external power source 103 can be portable for ease of use.

During at least some procedures, an external stimulator or trial modulator 105 can be coupled to the signal delivery device 110 during an initial procedure, prior to implanting the signal generator 101. For example, a practitioner (e.g., a physician and/or a company representative) can use the trial modulator 105 to vary the therapy parameters provided to the signal delivery device 110 in real time, and select optimal or particularly efficacious parameters. These parameters can include the location from which the electrical signals are emitted, as well as the characteristics of the electrical signals provided to the signal delivery device 110. In a typical process, the practitioner uses a cable assembly 120 to temporarily connect the trial modulator 105 to the signal delivery device 110. The practitioner can test the efficacy of the signal delivery device 110 in an initial position. The practitioner can then disconnect the cable assembly 120 (e.g., at a connector 122), reposition the signal delivery device 110, and reapply the electrical therapy. This process can be performed iteratively until the practitioner obtains the desired position for the signal delivery device 110. Optionally, the practitioner may move the partially implanted signal delivery element 110 without disconnecting the cable assembly 120. Furthermore, in some embodiments, the iterative process of repositioning the signal delivery device 110 and/or varying the therapy parameters may not be performed.

After a trial period with the trial modulator 105, the practitioner can implant the implantable signal generator 101 within the patient 190 for longer term treatment. The signal delivery parameters provided by the signal generator 101 can still be updated after the signal generator 101 is implanted, via a wireless physician's programmer 117 (e.g., a physician's laptop, physician's remote, etc.) and/or a wireless patient programmer 106 (e.g., a patient's laptop, a patient's remote, etc.). Generally, the patient 190 has control over fewer parameters than does the practitioner.

Figure 2:
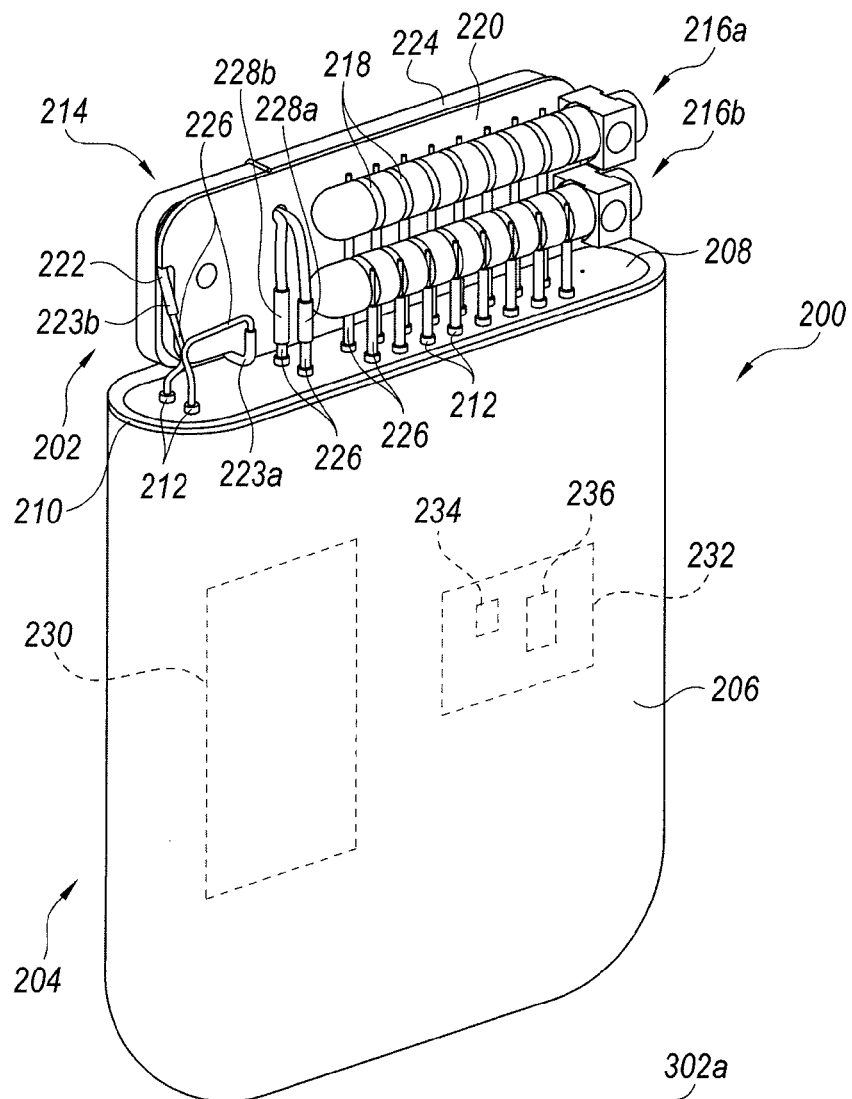
FIG. 2 is a partially schematic isometric view of an implantable signal generator having a header and a can configured in accordance with a further embodiment of the present technology.

FIG. 2 is a partially schematic isometric view of an implantable signal generator 200 having a header portion or header 202 and a can 204 configured in accordance with an embodiment of the present technology. The can 204 may include a rounded rectangular shell 206 and an oval shaped lid 208. In one embodiment, the shell 206 and the lid 208 can be titanium, and a weld joint 210 can join the lid 208 to the shell 206. In other embodiments, the shell 206 and the lid 208 can be made of other metals or metal alloys, or plastic, and can be joined together by other methods including press fitting, adhesive materials and/or threaded connections. In any of these embodiments, the lid 208 can include a plurality of feed-throughs 212 for electrical communication between the header 202 and the can 204.

The header 202 can include a charging and communication assembly 214, a first receiving element 216a and a second receiving element 216b (collectively, receiving elements 216). The receiving elements 216 can include a plurality of output terminals or contact assemblies 218, configured to provide electrical connections to the signal delivery device 110 (FIG. 1) or the lead extension 102 (FIG. 1). The charging and communication assembly 214 can include a support element 220 carrying a communication antenna 222 and a charging coil 224. The communication antenna 222 includes curved connectors 223 (identified individually as a first curved connector 223a and a second curved connector 223b). The support element 220, the communication antenna 222 and the charging coil 224 can be shaped, positioned, and/or otherwise configured to enhance the performance of the implantable signal generator, while fitting within the confines of the header 202 as will be described further below. Multiple wires 226 can extend upwardly from the can 204 through the feed-throughs 212 and couple to (a) individual contact assemblies 218, (b) the curved connectors 223, and (c) the charging and communication assembly 214 via bushings 228 (identified individually as a first bushing 228a and a second bushing 228b).

The wires 226 can provide electrical connections between components within the header 202, e.g., the charging coil 224 and the communication antenna 224, and components within the can 204, e.g., a battery 230, a controller 232, etc. The battery 230 can be electrically coupled to the controller 232 and the output terminals or contact assemblies 218 to provide electrical power to the implantable signal generator 200 via the receiving elements 216. The battery 230 can be recharged via an electrical coupling to the charging coil 224. The controller 232 can be electrically coupled to the contact assemblies 218 and the battery 230, and can include a processor 234, memory 236, electronic circuitry, and electronic components for controlling and/or operating the implantable signal generator. Computer readable instructions contained in the memory 236 can include operating parameters and instructions that can control the operation of the implantable signal generator 200. In operation, the charging coil 224 can convert electromagnetic energy (e.g., a magnetic flux) into electrical current to charge the battery 230. The communication antenna 224 can receive signals related to operation and control of the implantable signal generator 200. For example, control signals to update operating parameters (e.g., the frequency or duration of modulation signals) for the implantable signal generator 200 can be received by the communications antenna 224 and sent to the controller 232. The controller 232 can control the delivery of electrical power to the receiving elements 216.

Figure 3:
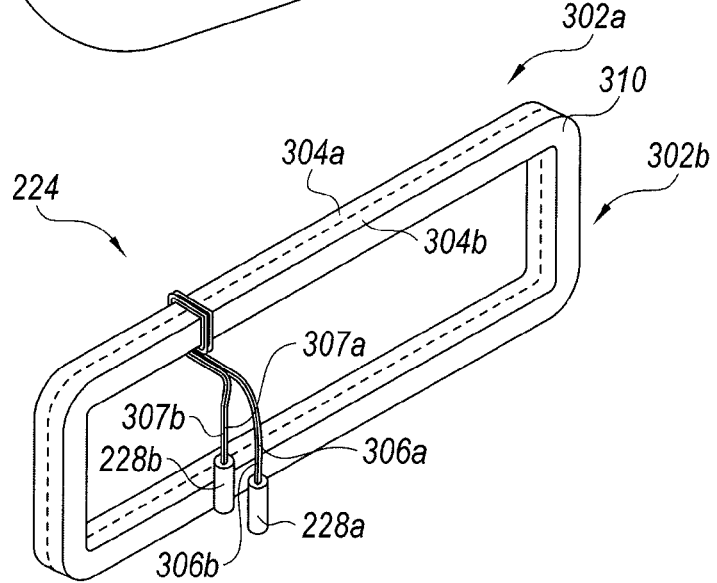
FIG. 3 is an isometric view of a charging coil having a pair of wire loops in accordance with another embodiment of the present technology.

FIG. 3 is an isometric view of a representative charging coil 224 having a pair of wire loops 302 (identified individually as a first wire loop 302a and a second wire loop 302b) in accordance with another embodiment of the present technology. Each of the wire loops 302 can be formed from a wire 304 (identified individually as a first wire 304a and a second wire 304b). The first wire 304a and the second wire 304b can be made from a variety of suitable metals or metal alloys (e.g., copper, silver coated copper, gold coated copper, gold, silver, platinum and/or other suitable metals or metal alloys). The first wire 304a has a first end 306a and a second end 307a. Similarly, the second wire 304b has a first end 306b and a second end 307b. The first end 306a of the first wire 304a and the first end 306b of the second wire 304b are crimped together at the first bushing 228a. The second end 307a of the first wire 304a and the second end 307b of the second wire 304b are crimped together at the second bushing 228b. Accordingly, the two loops 302a, 302b are connected in parallel. Although the illustrated embodiment includes two wires 304, other embodiments can include additional wires, and/or filers, and/or multi-filer wires, and/or a Litz wire having individually insulated wires that can be woven or braided into a bundle. For example, in one embodiment, one or more wire loops can include four wires or filers, rather than the two wires 304 shown in the illustrated embodiment.

The wire loops 302 can be formed by wrapping the first wire 304a around a spindle (not shown) multiple times, removing the spindle, wrapping the second wire 304b around a spindle multiple times, removing the spindle, laying the resulting wire loops 302a and 302b next to each other, and coating the wire loops 302 with an insulator 310. In other embodiments, the first wire 304a and the second wire 304b can be concurrently wrapped around the spindle, with the resulting wire loops having the first wire 304a and the second wire 304b in contact with each other along the entire lengths of the wires 304a, 304b. In any of these embodiments, the first ends 306a, 306b and the second ends 307a, 307b can be wrapped around the wire loops 302 to hold the wire loops 302a, 302b together, and the wire loops 302 can be coupled to the support element 220 (FIG. 2), as will be described further below.

Single wire loops that are used for inductive power generation can create increased heat due to electromagnetic properties inherent in inductive charging (e.g., the skin effect). By using multiple wires and loops, the skin effect can be reduced, causing a subsequent reduction in heat generation and/or a corresponding increase in the inductive charging capability. In some embodiments, the charging coil can have a resistance chosen to reduce the skin effect. For example, in one embodiment, a charging coil can have a resistance in the range of 2 ohms to 10 ohms. In other embodiments, charging coils can have a resistance that is greater than 10 ohms or less than 2 ohms. In particular embodiments, the pair of wires 304 may be wrapped around the spindle a specific number of times to enhance the performance of the charging coil 224 based on the size, shape and/or electromagnetic characteristics of the implantable signal generator 200 (FIG. 2), the external power source 103 (FIG. 1) and/or other components of the patient system 100 (FIG. 1). For example, in one embodiment, each wire 304 may be wrapped around the spindle 30 times. In other embodiments, the wires 304 may be wrapped around the spindle more or fewer times.

The charging coil 224 can be shaped to provide desired operational characteristics and to fit within the header 202 (FIG. 2). Accordingly, the support element 220 (FIG. 2) can be shaped in a corresponding manner to support the charging coil 224 and enable a secure coupling between the support element 220 and the charging coil 224. In the illustrated embodiment of FIG. 3, the charging coil 224 has a generally rectangular shape corresponding to the shape of the header 202, and a portion of the support element 220 (FIG. 2) corresponds to (e.g., closely matches) this rectangular shape. In other embodiments, the charging coil 224 and/or the support element 220 can have other shapes (e.g., circular, square, oval) to enhance the performance and/or fit of the charging coil 224 within the header 202 of the implantable signal generator 200 (FIG. 2).

Figure 4:
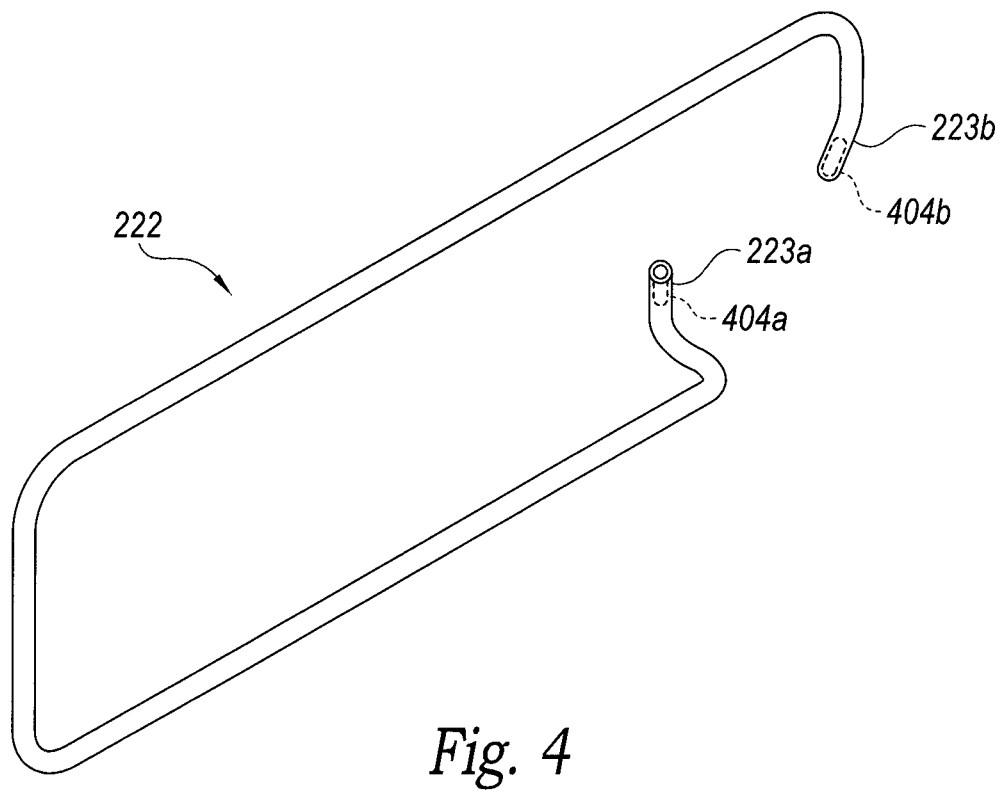
FIG. 4 is an isometric view of a communication antenna having curved connectors configured in accordance with a further embodiment of the present technology.

FIG. 4 is an isometric view of a representative communication antenna 222 having curved connectors 223a, 223b configured in accordance with a further embodiment of the present technology. The communication antenna 222 can be made from a variety of metals or metal alloys (e.g., copper, silver coated copper, gold coated copper, gold, silver, platinum and/or other suitable metals or metal alloys). In one embodiment, the communication antenna 222 can be made from magnet wire that is bent or otherwise formed into the rounded rectangular shape shown in FIG. 4. The communication antenna 222 can be shaped to provide particular communication capabilities and to fit within the implantable signal generator 200 (FIG. 2). The support element 220 (FIG. 2) can be shaped to correspond to (e.g., closely match) the shape of the communication antenna 222, and the curved connectors 223a, 223b can wrap around the support element 220, as will be described further below. The first curved connector 223a can include a first receiving cavity 404a and the second curved connector 223b can include a second receiving cavity 404b. The first receiving cavity 404a and the second receiving cavity 404b (collectively, the receiving cavities 404) can each be configured to individually receive an individual wire 226 (FIG. 2), as will be described further below.

Figure 5:
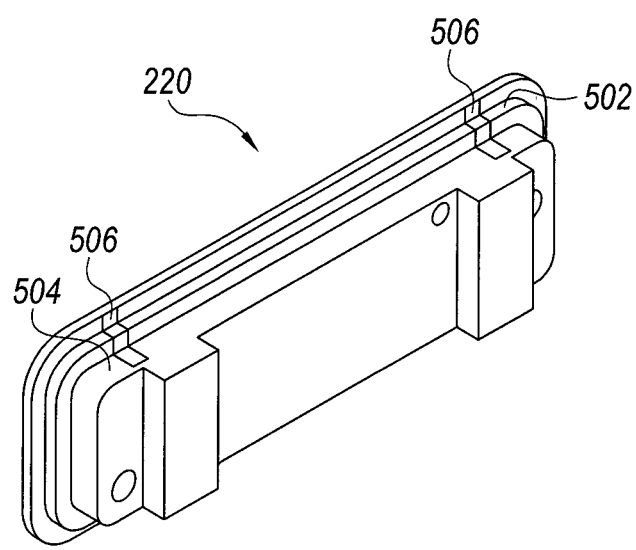
FIG. 5 is an isometric view of a support element having a first receiving surface and a second receiving surface in accordance with another embodiment of the present technology.

FIG. 5 is an isometric view of the support element 220, illustrating a first receiving surface 502 and a second receiving surface 504 positioned in accordance with an embodiment of the present technology. The first receiving surface 502 can be generally flat and can extend around the perimeter of the support element 220 in a shape that engages the communication antenna 222 (FIG. 4). Similarly, the second receiving surface 504 can be a generally flat surface and can extend around the perimeter of the support element 220 in a shape that supports the charging coil 224 (FIG. 3). The support element 220 can be molded from plastic or formed from other materials and shaped to support the communication antenna 222 (FIG. 4) and the charging coil 224 (FIG. 3). For example, the support element 220 can be made from silicone, an epoxy (e.g., epoxies manufactured by Hysol® or EPO-TEK®), Tecothane® and/or Delrin®. Adhesive elements 506 can be added to the first receiving surface 502 and/or the second receiving surface 504 to secure the communication antenna 222 (FIG. 4) and/or the charging coil 224 (FIG. 3).

Figure 6:
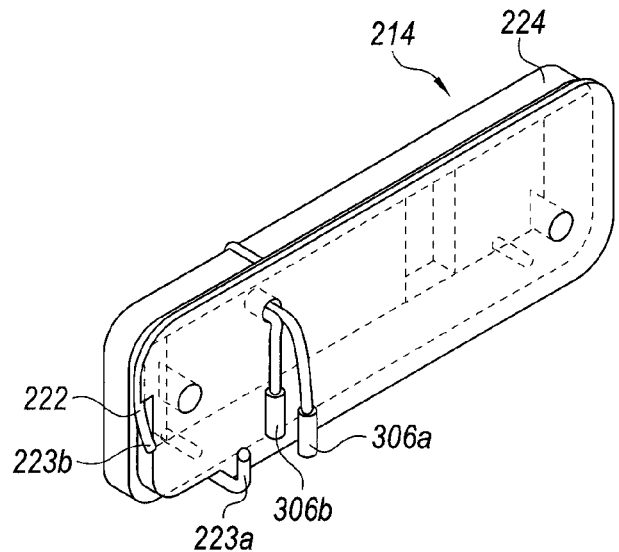
FIG. 6 is an isometric view of a charging and communication assembly having a communication antenna and a charging coil in accordance with an embodiment of the present technology.

FIG. 6 is an isometric view of a representative charging and communication assembly 214 including the communication antenna 222 and the charging coil 224, configured in accordance with an embodiment of the present technology. In the illustrated embodiment, the communication antenna 222 is engaged with the first receiving surface 502 (FIG. 5) and the curved connectors 223a, 223b are at least partially curved around a portion of the support element 220. The curved connectors 223a, 223b can be shaped and/or positioned to aid in relieving stress on the feed-throughs 212 (FIG. 2). The adhesive elements 506 (FIG. 5) aid in securing the communication antenna 222 and the charging coil 224 to the support element 220. Although the illustrated embodiment includes the charging coil 224 and the communication antenna 222 secured to the support element 220 with adhesive elements and/or curved connectors, in other embodiments, other fasteners or features can provide for this function. For example, fastening clips or tabs can be screwed or otherwise fastened to the support element 220 and can engage the communication antenna 222 and/or the charging coil 224. The support element 220 can be molded or formed to have grooves and/or flexible tabs that can secure the communication antenna 222 and/or the charging coil 224.

Referring to FIG. 2 and FIG. 6 together, the communication antenna 222 and the charging coil 224 carried by the support element 220 can be coupled to electrical components within the can 204 by connecting individual wires 226 to the curved connectors 223a, 223b and the bushings 228. The wires 226 that connect to the curved connectors 223a, 223b can be bent, as shown in FIG. 2, to align with the curved connectors 223a, 223b. The wires 226 can hold the support element 220 and the receiving elements 216 in the position shown in FIG. 2. The header 202 (FIG. 2) can undergo further processing to enclose the support element 220 and at least a portion of the receiving elements 216. For example, the header 202 can be at least partially immersed or encased in epoxy to seal the support element 220, the wires 226, the bushings 228, the charging coil 224, the communication antenna 222 and at least a portion of the receiving elements 216.

Figure 7:
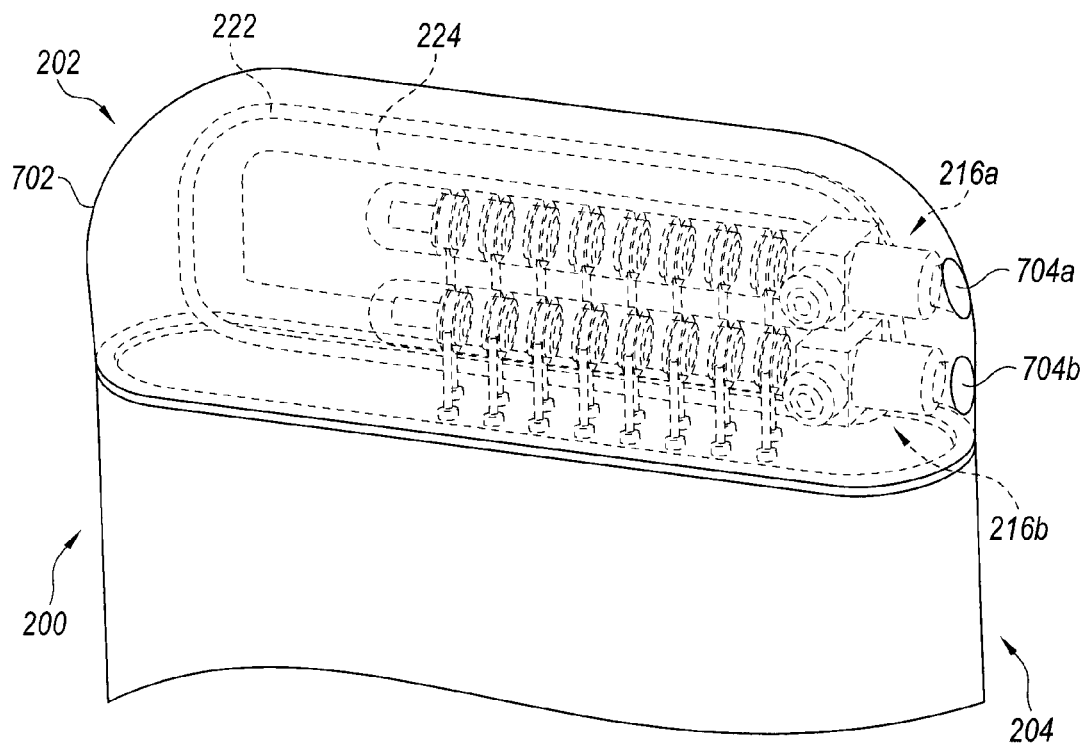
FIG. 7 is an isometric view of a portion of an implantable signal generator having a header configured in accordance with a further embodiment of the present technology.

FIG. 7 is an isometric view of a portion of the implantable signal generator 200 with a header 202 configured in accordance with a further embodiment of the present technology. In the illustrated embodiment, the header 202 includes an epoxy volume 702 having receiving inlets 704 (identified individually as a first receiving inlet 704a and a second receiving inlet 704b). The receiving inlets 704 provide access to the receiving elements 216a, 216b, thus allowing a lead 111 (FIG. 1) or a lead extension 102 (FIG. 1) to be connected to the signal generator 200. The epoxy volume 702 and the receiving inlets 704 can be formed in any of a variety of suitable manners. For example, the epoxy volume 702 and the receiving inlets 704 can be formed by placing a temporary plug (not shown) in each individual receiving element 216 and immersing the header 202 in epoxy (e.g., an epoxy filled mold). In other embodiments, the header 202 can be encased in other materials, including molded plastic. In some embodiments, the header 202 can be encased using casting and/or pre-molding methods.

Figure 8A:
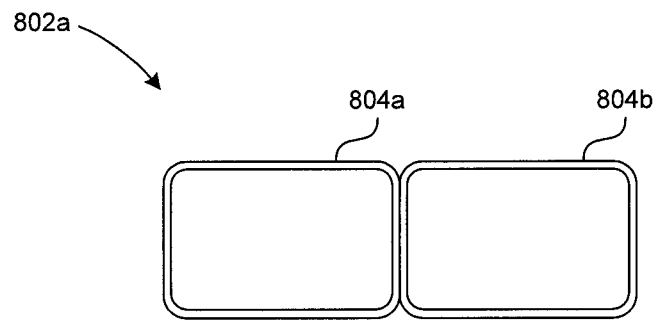
FIGS. 8A-8D schematically illustrate charging coils configured in accordance with other embodiments of the present technology.

Embodiments in accordance with the present technology can include charging coils and communication antennas shaped and configured in a variety of suitable manners. FIGS. 8A-8D schematically illustrate charging coils configured in accordance with other embodiments of the present disclosure. For example, FIG. 8A shows a charging coil 802a having a first wire loop 804a and a second wire loop 804b (collectively, wire loops 804) in a side by side, rectangular configuration. In the embodiment shown, wire loops 804a and 804b have matching sizes and shapes. However, in alternative embodiments, wire loops 804a and 804b may differ in size and shape. The size, shape, and location of wire loops 804 may be configured to optimize battery charging parameters. For example, in one embodiment, charging coil 802a is configured to provide daily charging for an implantable signal generator configured to provide high frequency therapy signals (e.g., therapy signals at a frequency in a frequency range of from about 1.5 kHz to about 100 kHz, and current amplitudes in a range of from about 0.1 mA to about 20 mA).

Figure 8B:
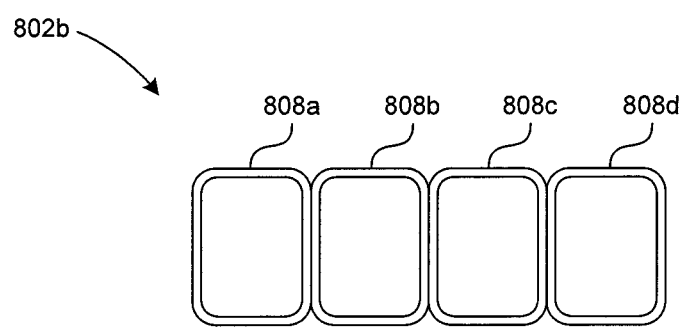

FIG. 8B shows a charging coil 802b having a plurality of wire loops 808 (identified individually as a first wire loop 808a, a second wire loop 808b, a third wire loop 808c and a fourth wire loop 808d). In the embodiment shown, wire loops 808a, 808b, 808c, and 808d have matching sizes and shapes. However, in alternative embodiments, one or more of wire loops 808a, 808b, 808c, and 808d may differ in size and shape. The size, shape, and location of wire loops 808 may be configured to optimize battery charging parameters. For example, in one embodiment, charging coil 802b is configured to provide daily charging for an implantable signal generator configured to provide high frequency therapy signals (e.g., therapy signals at a frequency in a frequency range of from about 1.5 kHz to about 100 kHz, and current amplitudes in a range of from about 0.1 mA to about 20 mA).

Figure 8C:
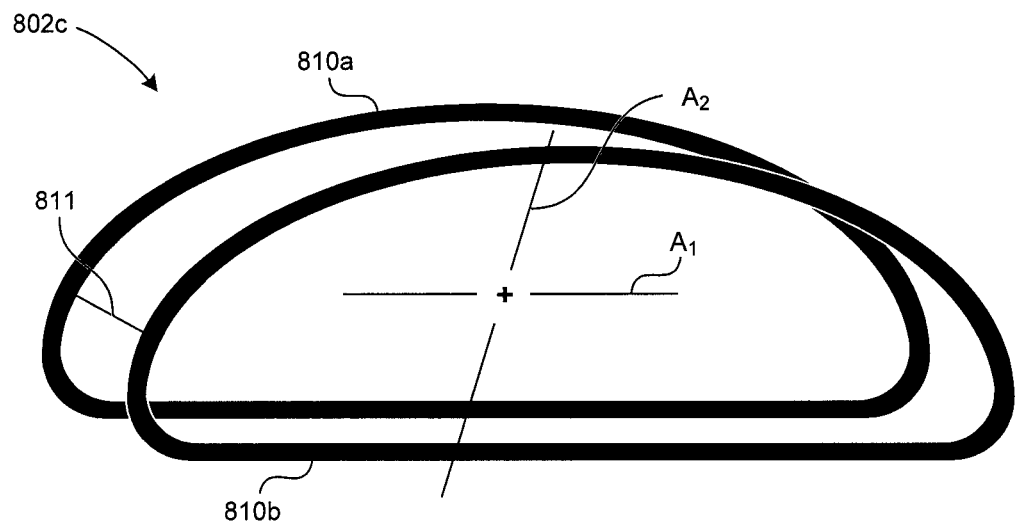

FIG. 8C shows a charging coil 802c having a first wire loop 810a and a second wire loop 810b (identified collectively as wire loops 810) in an offset, parallel plane, hemisphere-shaped configuration. The charging coil 802c can include one or more wires 811 that form the wire loops 810 and can connect the first wire loop 810a to the second wire loop 810b. The first wire loop 810a and the second wire loop 810b can be offset along a first axis A1 and along a second axis A2 such that the first wire loop 810 is in a first plane, and the second wire loop 810b is in a second plane, different from the first plane. In the embodiment shown, wire loops 810a and 810b have matching sizes and shapes. However, in alternative embodiments, the wire loops 810a and 801b may differ in size and shape. The size, shape, and location of wire loops 810 may be configured to optimize battery charging parameters. For example, in one embodiment, charge coil 802c is configured to provide daily charging for an implantable signal generator configured to provide high frequency therapy signals (e.g., therapy signals at a frequency in a frequency range of from about 1.5 kHz to about 100 kHz, and current amplitudes in a range of from about 0.1 mA to about 20 mA).

Figure 8D:
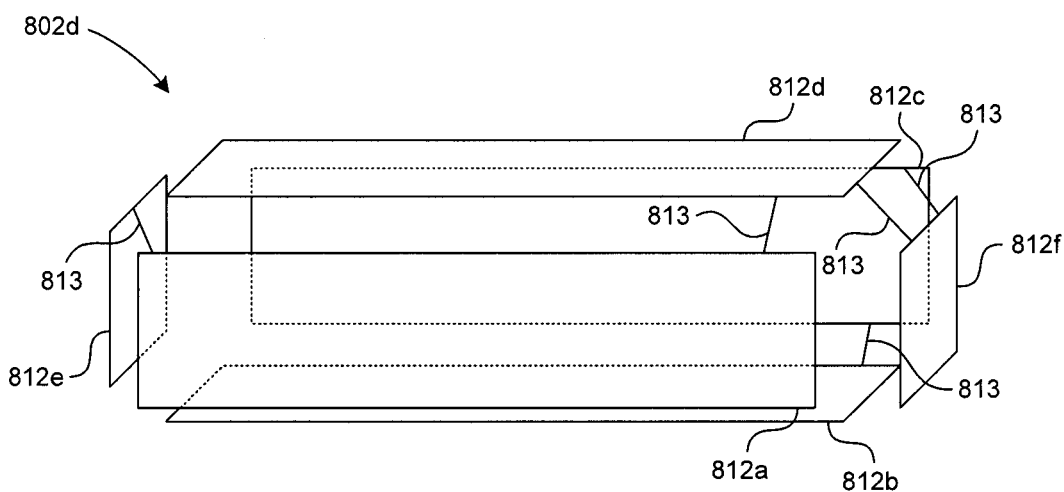

FIG. 8D shows a charging coil 80d having six wire loops 812 (identified individually as wire loops 812a-812f) arranged in a rectangular cube. In a manner similar to the charging coil 802c, the charging coil 802d can include one or more wires 813 that form the wire loops 812 and can connect the wire loops 812. The size, shape, and location of wire loops 812a-812f may be configured to optimize battery charging parameters. For example, in one embodiment, the charging coil 802d is configured to provide daily charging for an implantable signal generator configured to provide high frequency therapy signals (e.g., therapy signals at a frequency in a frequency range of from about 1.5 kHz to about 100 kHz, and current amplitudes in a range of from about 0.1 mA to about 20 mA).

The charging coils 802a-802d provide improved charging capabilities as a result of the relative positions of the respective wire loops within an implantable signal generator. For example, the offset position of the wire loops 810 of the charging coil 802c can allow space for other components while providing a large overall cross-sectional area to increase the rate at which energy is transferred to the charging coil 802c. Additionally, the six wire loops 812a-812f of the charging coil 802d are positioned to face six different directions, and can thereby interact with magnetic fields directed at the charging coil 802d from any of a variety of different directions. Although the charging coils 802a-802d include wire loops that are in the same plane, in parallel planes, or in orthogonal planes, charging coils in accordance with the present technology can include wire loops that are positioned in planes at a variety of suitable non-zero angles. Additionally, the charging coils 802a-802d can include more or fewer wire loops 804, 808, 810 and 812 in a variety of shapes and sizes (e.g., circular, oval, square). In one embodiment, charging coils 802a, 802b, 802c, 802d, or equivalents thereof, are sized, shaped, located within an implantable signal generator header, and/or otherwise configured to provide means for charging a battery of an implantable signal generator to provide at least 12 operational hours (and preferably at least 24 operational hours) in the delivery of high frequency therapy signals at a frequency in a frequency range of from about 1.5 kHz to about 100 kHz, and current amplitudes in a range of from about 0.1 mA to about 20 mA.

Figure 9:
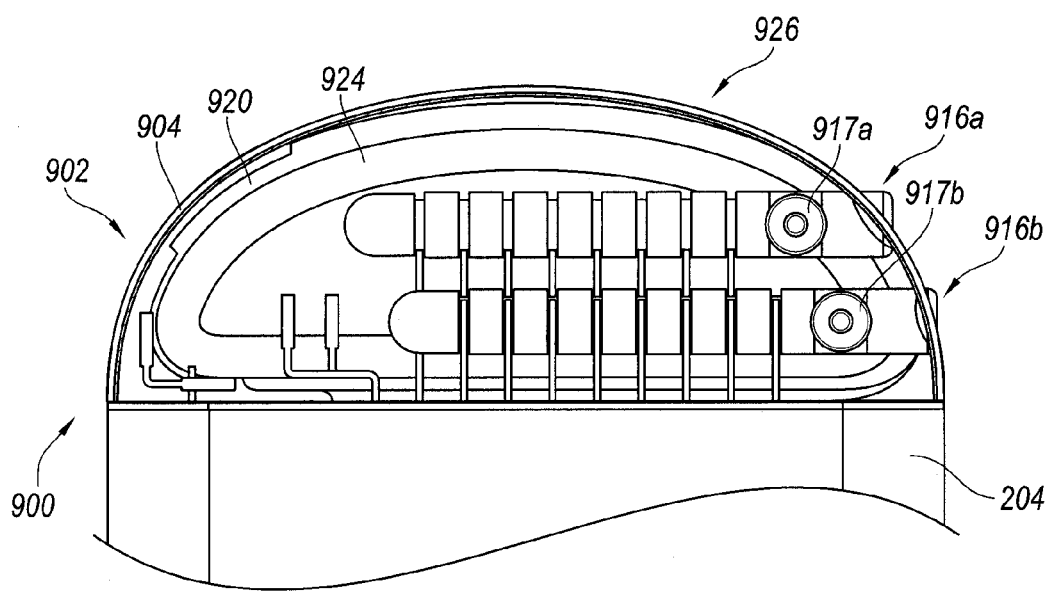
FIG. 9 is a partially cutaway side view of a portion of an implantable signal generator having a header configured in accordance with a further embodiment of the present technology.

For example, FIG. 9 is a partially cutaway side view of a portion of an implantable signal generator 900 for delivering therapy signals, with a header 902 configured in accordance with an embodiment of the present technology. In the illustrated embodiment, a charging coil 924, a support element 920, and a pair of receiving elements 916 (identified individually as a first receiving element 916a and a second receiving element 916b) are positioned within a header cap 904. The header cap 904 can be formed from any of a variety of suitable materials. For example, in some embodiments, the header cap 904 can be formed from epoxy in a manner at least generally similar to that described above with respect to FIG. 7. In other embodiments, the header cap 904 can be pre-formed from Tecothane®, East-Eon™, silicone, and/or any other suitable material and can be attached to the can 204 to encompass the components within the header 902.

The receiving elements 916 can be positioned within the header 902 such that the receiving elements 916 are at least generally flush with a curved upper surface 926 of the header 902. For example, because the respective receiving elements 916a, 916b are positioned at different locations with respect to the curvature of the surface 926, the first receiving element 916a is offset from the second receiving element 916b, such that the receiving elements 916 align with the curved surface 926. In some embodiments, the charging coil 924 can be shaped to at least partially match the shape of the header 902. For example, in the illustrated embodiment, the charging coil 902 includes a hemispheric or "D" shape that closely matches the shape of the header 902. Matching the shape of the charging coil 924 to the shape of the header 902 increases the cross-sectional area of the charging coil 924 and increase the charging performance, thereby facilitating the battery charging for high-demand implantable signal generators, such as signal generators configured to deliver high frequency therapy.

The header 902 includes a first access seal 917a and a second access seal 917b (collectively referred to as the access seals 917). The access seals 917 include a self-sealing entrance point to provide access for a tool (e.g., a screwdriver) to secure a connection (e.g., a screw) to the signal delivery device 110 (FIG. 1) or the lead extension 102 (FIG. 1). The access seals 917 can be formed from a pliable silicone or other suitable material such that the tool can pass through and expand the entrance point. When the tool is withdrawn, the entrance point can automatically close to reduce or eliminate the possibility of any subsequent entrance of foreign material (e.g., blood or other bodily fluids) into the header 902.

Figure 10:
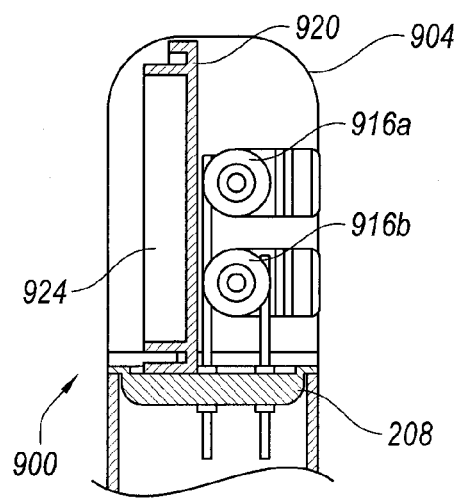
FIG. 10 is a cross-sectional end view of a portion of an implantable signal generator configured in accordance with an embodiment of the present technology.

FIG. 10 is a cross-sectional end view of a portion of the implantable signal generator 900 configured in accordance with an embodiment of the present technology. In the illustrated embodiment, the support element 920 is attached to the lid 208 and carries the charging coil 924. Similar to the support element 220, the support element 920 can be made from variety of suitable materials (e.g., silicone, an epoxy (e.g., epoxies manufactured by Hysol® or EPO-TEK®), Tecothane® and/or Delrin®). The receiving elements 916 and an antenna (not shown) can be attached to the support element 920. The support element 920 can maintain the position of the charging coil 924, the antenna, and/or the receiving elements 916 while the header cap 904 is formed and/or positioned on the implantable signal generator 900.

Figure 11A:
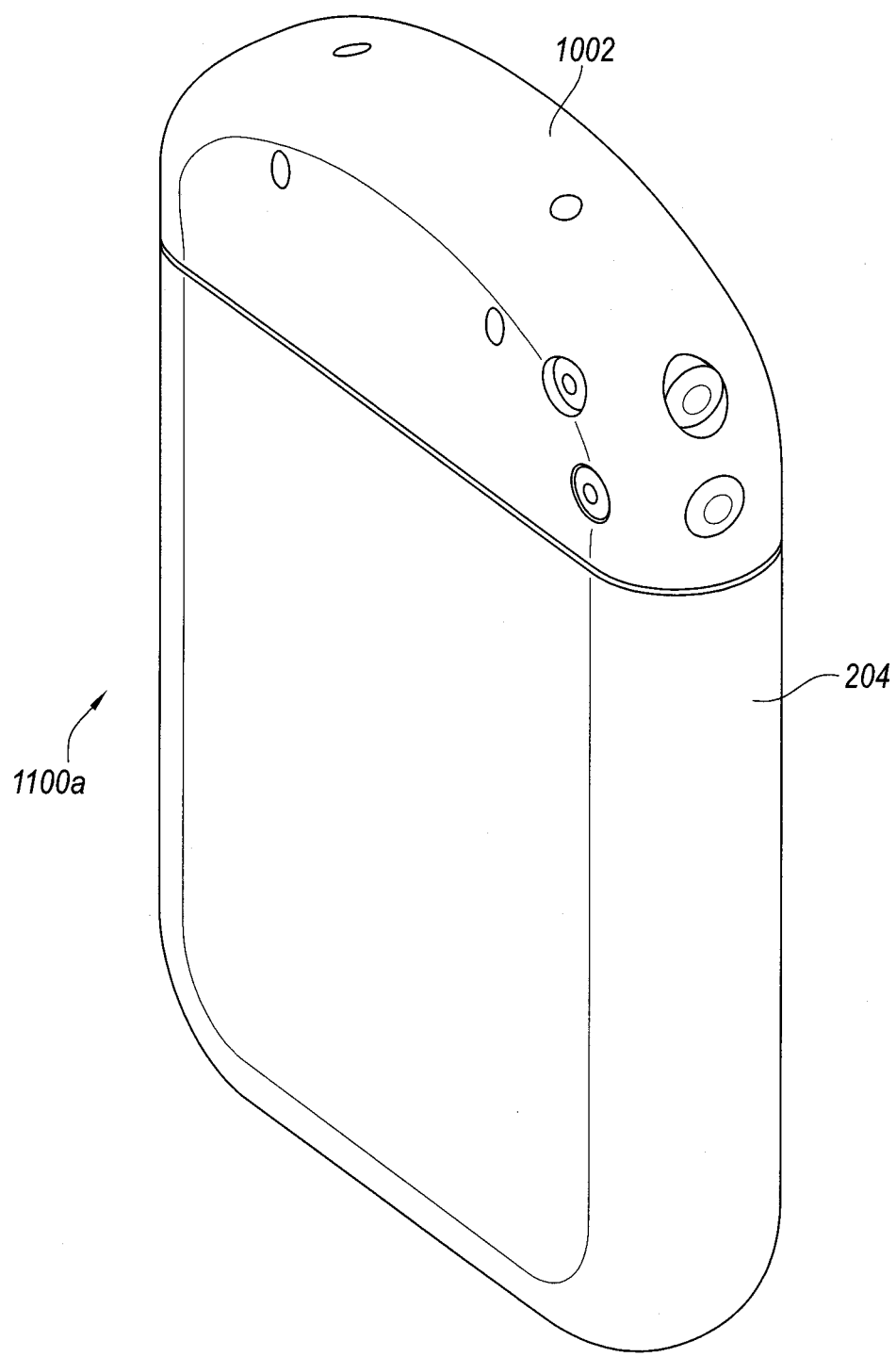
FIGS. 11A and 11B are isometric views of implantable signal generators configured in accordance with embodiments of the present technology.
Figure 11B:
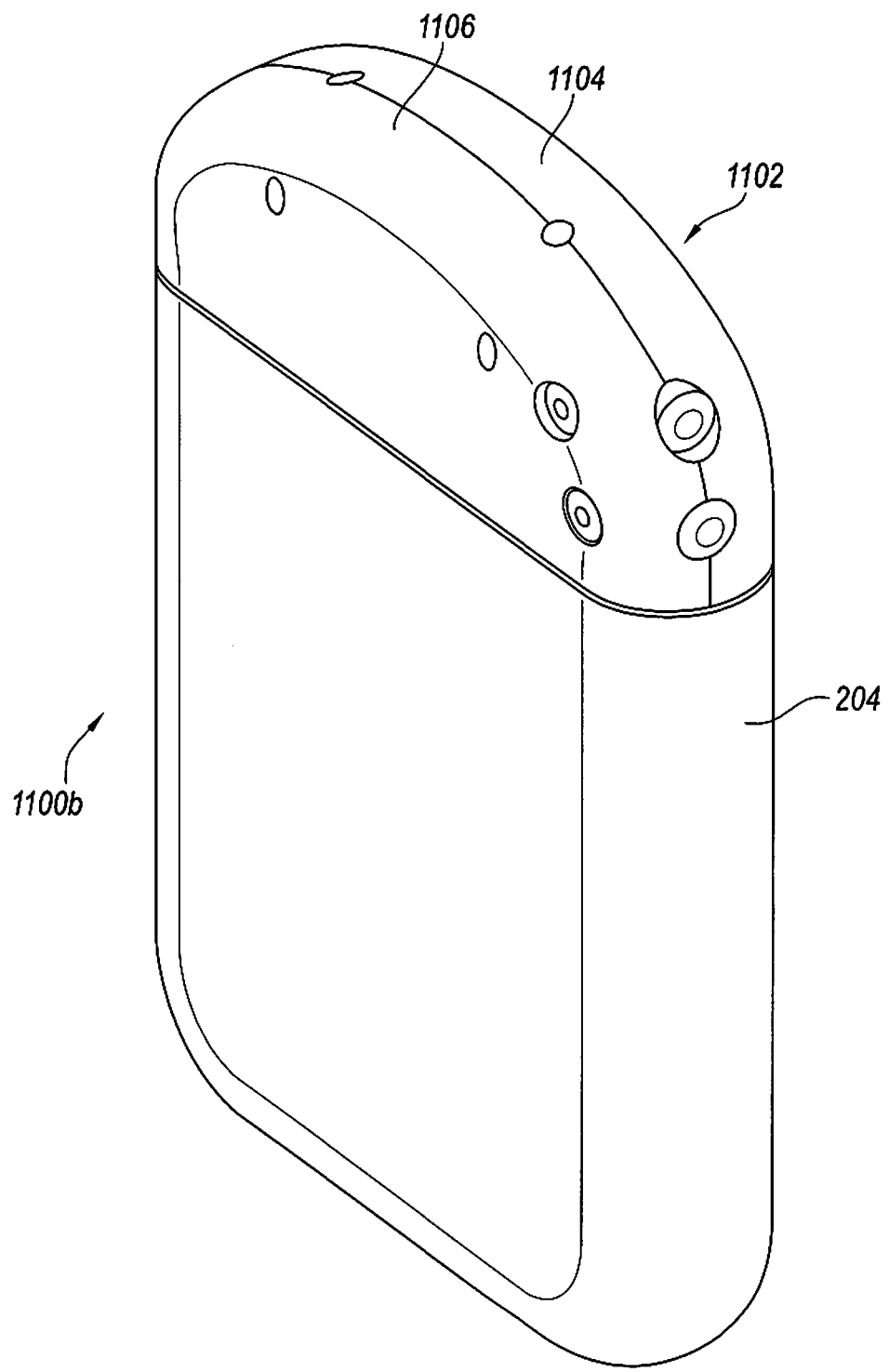

FIGS. 11A and 11B are isometric views of implantable signal generators 1100a and 1100b, respectively, configured in accordance with embodiments of the present technology. The implantable signal generator 1100a of FIG. 11A includes a unitary header cap 1002. The implantable signal generator 1100b of FIG. 11B includes a two-piece header cap 1102 having a first portion 1104 and a second portion 1106. Similar to the header cap 904, the header caps 1002 and 1104 can be formed from epoxy or can be pre-formed from Tecothane®, Elast-Eon™, silicone or other materials. The header caps 1002 and 1104 can be attached to the can 204 in a variety of suitable manners. For example, in one embodiment, the header caps 1002, 1102 can be attached to the lid 208 (not visible in FIGS. 11A and 11B) with an adhesive. In other embodiments, the lid 208, the can 204 and/or other components can include a groove and the header cap 1102 can include a ring that can engage the groove.

Figure 12:
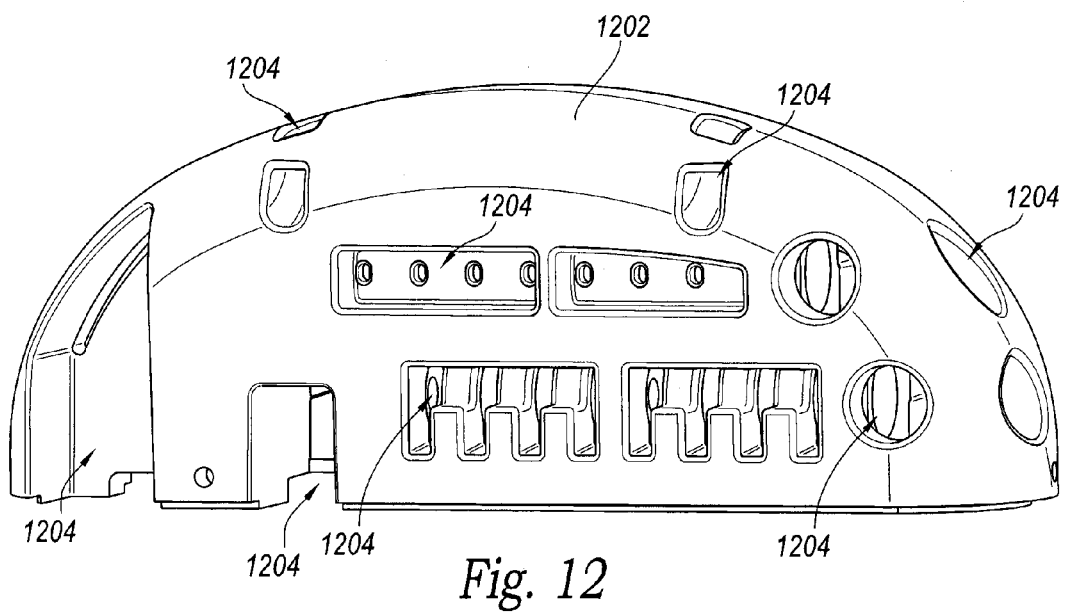
FIG. 12 is an isometric view of a pre-molded header cap configured in accordance with an embodiment of the present technology.

FIG. 12 is an isometric view of a pre-molded header cap 1202 configured in accordance with an embodiment of the present technology. In the illustrated embodiment, the header cap 1202 includes a plurality of cutouts or openings 1204. The openings 1204 can be shaped to accommodate various components that can be positioned within the header cap 1202 (e.g., receiving elements, charging coils, antennae, etc.). In some embodiments, components can be inserted into the header cap 1202 and the header cap 1202 can maintain the components in a desired position during subsequent attachment to the can 204.

Although the charging coils and communication antennas discussed above have been described as separate components, in other embodiments the functions provided by these components can be performed by the same element or elements. For example, both the charging and communications can be performed by the same coil/antenna, e.g., if the frequency used to charge and communicate signals is the same, approximately the same, generally similar or otherwise compatible. The coil/antenna can include a single loop or multiple loops, as described above.

One feature of at least some of the foregoing embodiments is that the charging coils and the communications antennae are positioned in the headers. An additional advantage of this feature is that it can reduce the manufacturing complexity and the associated cost of producing the implantable signal generator. For example, the charging coils of existing signal generators are often located in a compartment (e.g., a container or pouch) coupled to an external surface of the can. Having an external compartment necessitates additional fabrication and processing steps to form the compartment and requires additional electrical connections between the compartment and the header and/or additional penetrations through the side of the can to accommodate electrical connections. In embodiments of the present disclosure, the header can house all of the permanent electrical connections that are external to the can, and all of the external components can be encased in one operation (e.g., forming the epoxy volume or attaching the header cap). Accordingly, implantable signal generators in accordance with embodiments of the present technology can provide several advantages over existing devices.

In some embodiments, the charging coil has an operational range of three to four centimeters. Accordingly, the charging coil can be separated from the external power source by up to three to four centimeters during charging. The communications antenna can have an operational range of 60 centimeters or more, facilitating transmission between the communications antenna and the wireless physician's programmer and/or the wireless patient programmer within this range. Accordingly, the implantable signal generator can be implanted with the charging coil located closer to the patients skin than is the communications antenna, to accommodate the shorter operational range of the charging coil. In some embodiments, this configuration can enhance (e.g., optimize) the charging capability of the implantable signal generator. In other embodiments, the implantable signal generator can be implanted with the charging coil more distal from the patients skin relative to the communications antenna.

Regardless of the location within a patient, the implantable signal generators described herein provide enhanced charging and communication capabilities over other devices. For example, the location of the charging coil within the header reduces interference or attenuation that can occur with charging coils that are located within the can or attached to the can. For example, electromagnetic signals from an external power source that are directed to the charging coil are less likely to be inadvertently absorbed by the can. Locating the charging coil in the header can also reduce the heat generated by the electromagnetic induction of the charging process. For example, the external power source can be positioned primarily over the header, and not the can, so that the amount of energy generated by the external power source and absorbed by the can may be reduced, thereby reducing unwanted induction and heat generation in the can.

In addition to or in lieu of the above advantages, the reduced interference and enhanced charging and communication capabilities of devices in accordance with the present technology can provide greater flexibility for the practitioner who positions the implantable signal generator within a patient. Existing signal generators often require the charging coil to be positioned proximal to a patient's skin relative to other components. For example, signal generators having charging coils located in a compartment on the external surface of the can generally have to be implanted with the compartment facing the patient's skin. This limitation can reduce the ability of a practitioner to position the signal generator to optimize connections to other components. For example, the practitioner may have to route leads or other electrical connections a further distance because the signal generator cannot be "flipped" to provide connections on the preferred side of an implantation site. In several of the embodiments of the present technology, a practitioner can position the implantable signal generator with the receiving inlets facing a chosen direction, without regard for the relative proximity of the charging coil or the communications antenna to the patient's skin. Accordingly, the reduced interference and enhanced charging capabilities of the present technology provide for greater implantation options.

In addition to the advantages discussed above, implantable signal generators and/or charging coils in accordance with the present technology can be particularly beneficial for systems employing high frequency modulation. For example, the signals and operational parameters of high frequency systems can require greater power usage than traditional SCS systems. The increased charging efficiency of the present technology can help meet greater power requirements without necessitating longer charge times. Accordingly, several embodiments in accordance with the present technology can be combined with high frequency modulation systems, including those described in U.S. patent application Ser. No. 12/264,836, filed Nov. 4, 2008, and titled MULTI-FREQUENCY NEURAL TREATMENTS AND ASSOCIATED SYSTEMS AND METHODS; U.S. patent application Ser. No. 12/765,747, filed Apr. 22, 2010, and titled SELECTIVE HIGH-FREQUENCY SPINAL CORD MODULATION FOR INHIBITING PAIN WITH REDUCED SIDE EFFECTS AND ASSOCIATED SYSTEMS AND METHODS; and U.S. patent application Ser. No. 13/607,617, filed Sep. 7, 2012, and titled SELECTIVE HIGH FREQUENCY SPINAL CORD MODULATION FOR INHIBITING PAIN, INCLUDING CEPHALIC AND/OR TOTAL BODY PAIN WITH REDUCED SIDE EFFECTS, AND ASSOCIATED SYSTEMS AND METHODS. The above referenced patent applications are incorporated herein by reference in their entireties.

Furthermore, several features of the embodiments described herein can provide additional synergistic effects in systems employing high frequency modulation. For example, four wire charging coils, copper alloy charging coils, the position of the charging coil and/or the antenna within a header of an implantable signal generator, and/or other features can provide synergistic affects for systems delivering high frequency signals for neural modulation.

From the foregoing, it will be appreciated that specific embodiments of the disclosed technology have been described herein for purposes of illustration, but that various modifications may be made without deviating from the technology. For example, rather than a single support element having external surfaces that support both the charging coil and the communication antenna, the charging coil and the communication antenna can be supported by individual structures having different shapes or configurations. In other embodiments, the charging coil and the communication antenna can be supported solely by wires extending from the can of the implantable signal generator, without a support element. Other materials may be used in place of those described herein, or additional components may be added or removed. For example, although the illustrated embodiments include a header having two receiving elements, other embodiments can include additional receiving elements, or other connectors. Additionally, any of the embodiments shown or described herein may be combined with each other as the context permits.

Additional Embodiments

In one embodiment, there is provided an implantable signal generator, comprising: (a) a can having an output terminal and a battery electrically coupled to the output terminal; and (b) a header portion adjacent the can and having a communication antenna, and a charging coil electrically coupled to the battery, wherein the charging coil is positioned to receive electromagnetic energy and direct electrical current to charge the battery, and wherein the communication antenna is positioned to receive external control signals. The implantable signal generator may further comprise: (c) a support element positioned in the header, wherein the charging coil and the communication antenna are connected to the support element. The charging coil may include a plurality of wire loops. A first wire loop may be positioned in a first plane and a second wire loop is positioned in a second plane, and wherein the second plane is different from the first plane. Alternatively, a first wire loop is positioned in a first plane and a second wire loop is positioned in a second plane, the first plane disposed at a non-zero angle with respect to the second plane.

The header portion may include: (i) a plurality of receiving elements positioned to provide electrical connections; and (ii) an epoxy volume at least partially encasing the receiving elements. The header may alternatively include a curved surface, and wherein the charging coil is shaped to at least partially match the curved surface.

The can may include a shell and a lid, the lid having a plurality of feed-throughs. The implantable signal generator may thus further comprise: a controller positioned within the can and configured to direct electrical signals to the output terminal; and a plurality of wires positioned to extend through the feed-throughs and operably couple the controller to the communication antenna and the battery to the charging coil.

In another embodiment, there is provided an implantable medical device for delivering electrical therapy signals to a patient's spinal region to alleviate pain. The medical device comprising: (a) a can having a shell and a lid, wherein the lid includes a plurality of feed-throughs; (b) an output terminal positioned to provide electrical power to a signal delivery device; (c) a controller disposed within the can and coupled to the output terminal to control electrical power directed to the output terminal; (d) a battery disposed within the can and coupled to the controller; (e) a plurality of wires, individual wires extending upwardly from the can through corresponding individual feed-throughs; (f) a header carried by the can; (g) a support element disposed within the header; (h) a charging coil having at least one wire loop, the charging coil being carried by the support element in the header such that the entirety of the wire loop is disposed outside of the can, and wherein the charging coil is operably coupled to the battery via at least one first individual wire; and (i) a communication antenna carried by the support element and operably coupled to the controller via at least one second individual wire. The charging coil may include a plurality of wire loops, wherein a first wire loop is offset from a second wire loop along both a first axis and a second axis orthogonal to the first axis. The charging coil may otherwise include a plurality of wire loops, wherein a first wire loop is positioned in a first plane and a second wire loop is positioned in a second plane, the first plane disposed at a non-zero angle relative to the second plane. The header may include a curved surface, wherein the charging coil is shaped to at least partially match the shape of the curved surface.

The medical device may further comprise a receiving element disposed in the header, wherein the header includes an epoxy volume and the receiving element is at least partially encased in the epoxy volume, the receiving element including the output terminal. The medical device may further comprise a header cap, wherein the support element is attached to the lid and configured to support the charging coil and the communication antenna.

In yet another embodiment, there is provided a method for forming an implantable signal generator, comprising: (a) forming a shell; (b) forming a lid having a plurality of feed-throughs; (c) attaching the lid to the shell; (d) forming a charging coil; (e) forming a communication antenna; and (f) positioning the communication antenna and the charging coil to be supported by the lid, external to the shell. The method may further comprise: (g) positioning a battery and a controller within the shell; (h) electrically coupling the charging coil to the battery; and (i) electrically coupling the communication antenna to the controller. The method may further comprise forming a header cap to encase the charging coil and the communication antenna. Forming the charging coil may include forming a plurality of wire loops, and wherein the method further may further comprise positioning a first wire loop in a first plane and positioning a second wire loop in a second plane, the first plane is disposed at a non-zero angle relative to the second plane. Alternatively, the method may further comprise forming a support element, wherein positioning the communication antenna and the charging coil to be supported by the lid includes attaching the communication antenna and the charging coil to the support element. The method may further comprise forming a header cap having a curved surface.

In still another embodiment, there is provided a spinal cord stimulation system for applying therapy signals to a patient's spinal region. The system comprising: an implantable signal generator having (a) a can (or housing) having an output terminal and a battery (disposed within the housing) electrically coupled to the output terminal; and (b) a header portion adjacent the can and having a communication antenna, and a charging coil electrically coupled to the battery. The charging coil is positioned (e.g., within the header portion outside of the can (or housing)) to receive electromagnetic energy (e.g., from an external power source) and direct electrical current to charge the battery. The communication antenna may be positioned (e.g., within the header portion outside of the can (or housing)) to receive external control signals. The implantable signal generator may further comprise: (c) a support element positioned in the header, wherein the charging coil and the communication antenna are connected to the support element. The charging coil may include a plurality of wire loops. A first wire loop may be positioned in a first plane and a second wire loop is positioned in a second plane, and wherein the second plane is different from the first plane. Alternatively, a first wire loop is positioned in a first plane and a second wire loop is positioned in a second plane, the first plane disposed at a non-zero angle with respect to the second plane.

The system further comprises at least one lead body connected to the implantable signal generator and having at least one electrode. In one embodiment, the implantable signal generator generates a high frequency therapy signal having a frequency in the range of from about 1,500 Hz to about 100,000 Hz for delivery through the lead body electrode. The high frequency range may alternatively be from about 2,500 Hz to about 20,000 Hz; or from about 3,000 Hz to about 10,000 Hz. The high frequency therapy signal may be biphasic, may be a sine wave or a square wave, and/or may be applied at a duty cycle of about 50% or less. The high frequency therapy signal may have a current amplitude in an amplitude range from about 0.1 mA to about 20 mA. The high frequency therapy signal may be applied in place of a low frequency stimulation signal to replace pain relief provided by paresthesia. In other words, the high frequency therapy signal may be applied to the patient's spinal cord region to alleviate pain without causing the patient to experience paresthesia. The implantable signal generator may generate the high frequency therapy signal for application directly to the dorsal column, the dorsal root, and/or the dorsal root ganglion. The implantable signal generator may be configured to adjust the high frequency therapy signal such that after the high frequency therapy signal has been initialized, an amplitude of the high frequency therapy signal is reduced from a first operating level to a second, lower operating level without affecting the sensory experience of the patient. For example, the amplitude of the high frequency therapy signal may be reduced by about 10-30% after initialization. The implantable signal generator may also be configured to apply the high frequency therapy signal in a discontinuous fashion so as to include periods when the high frequency therapy signal is applied, and periods when the high frequency therapy signal is terminated according to a duty cycle. The implantable signal generator may also be configured to generate a low frequency therapy signal to selectively induce paresthesia, wherein the low frequency therapy signal has a frequency in the range of up to about 1,500 Hz.

In one embodiment, one or more of the above-described headers are provided in a hemispherical (or sideways "D") shape attached to the top of the signal generator's can (or housing). The charge coil within the header is then configured to have a shape that at least partially follows (or matches) the shape of the header. As such, a hemispherically shaped header is matched with a hemispherically shaped charging coil.

In yet another embodiment, an implantable medical device includes a can having a shell and a lid, wherein the lid includes a plurality of feed-throughs. An output terminal can be positioned to provide electrical power to a signal delivery device and a controller can be positioned within the can and coupled to the output terminal to control electrical power directed to the output terminal. A battery disposed within the can can be coupled to the controller and a plurality of wires can extend upwardly from the can through corresponding individual feed-throughs. A header having a curved surface can be carried by the can and a support element can be positioned within the header. A charging coil having at least one wire loop can include four individual wires or filers. The wires or filers can include at least two of a) copper, b) silver, and c) gold. The charging coil can be carried by the support element in the header such that the entirety of the wire loop is disposed outside of the can, and the charging coil can be operably coupled to the battery via at least one first individual wire. The charging coil can have a resistance within the range of 2 ohms to 12 ohms, and a communication antenna can carried by the support element and operably coupled to the controller via at least one second individual wire.

While various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure and associated technology can encompass other embodiments not expressly shown or described herein.

We claim:

1. An implantable medical device for delivering electrical therapy signals to a patient's spinal region to alleviate pain, comprising:
 a can having a shell and a lid, wherein the lid includes a plurality of feed-throughs;
 an output terminal positioned to provide electrical power to a signal delivery device;
 a controller disposed within the can and coupled to the output terminal to control electrical power directed to the output terminal;
 a battery disposed within the can and coupled to the controller;
 a plurality of wires, individual wires extending upwardly from the can through corresponding individual feed-throughs;
 a header carried by the can;
 a support element disposed within the header;
 a charging coil having at least one wire loop, the charging coil being carried by the support element in the header such that the entirety of the wire loop is disposed outside of the can, wherein the charging coil is operably coupled to the battery via at least one first individual wire, and wherein the charging coil is configured to charge the battery with electrical current generated via electromagnetic induction; and
 a communication antenna carried by the support element and operably coupled to the controller via at least one second individual wire, wherein the communication antenna is configured to receive data transmitted to the implantable medical device via an electromagnetic signal.

2. The medical device of claim 1, wherein the charging coil includes a plurality of wire loops, and wherein a first wire loop is offset from a second wire loop along both a first axis and a second axis orthogonal to the first axis.

3. The medical device of claim 1, wherein the charging coil includes a plurality of wire loops, and wherein a first wire loop is positioned in a first plane and a second wire loop is positioned in a second plane, the first plane disposed at a non-zero angle relative to the second plane.

4. The medical device of claim 1, further comprising a receiving element disposed in the header, wherein the header includes an epoxy volume and the receiving element is at least partially encased in the epoxy volume, the receiving element including the output terminal.

5. The medical device of claim 1, wherein the header includes a curved surface, and wherein the charging coil is shaped to at least partially match the shape of the curved surface.

6. The medical device of claim 1 wherein the header includes a header cap that at least partially encloses the charging coil and the communication antenna, and wherein the support element is attached to the lid and configured to support the charging coil and the communication antenna.

7. An implantable signal generator, comprising:
a can having an output terminal and a battery electrically coupled to the output terminal; and
a header portion adjacent the can and having a plurality of receiving elements positioned to provide electrical connections; an epoxy volume at least partially encasing the receiving elements, a communication antenna, and a charging coil electrically coupled to the battery, wherein the charging coil is positioned to receive electromagnetic energy and direct electrical current to charge the battery, and wherein the communication antenna is positioned to receive external control signals.

8. An implantable signal generator, comprising:
a can having an output terminal and a battery electrically coupled to the output terminal; and
a header portion adjacent the can and having a communication antenna, and a charging coil electrically coupled to the battery, wherein the charging coil is positioned to receive electromagnetic energy and direct electrical current to charge the battery, wherein the communication antenna is positioned to receive external control signals, wherein the header includes a curved surface, and wherein the charging coil is shaped to at least partially match the curved surface.

9. An implantable signal generator, comprising:
a can having an output terminal and a battery electrically coupled to the output terminal, wherein the can includes a shell and a lid, the lid having a plurality of feed-throughs;
a header portion adjacent the can and having a communication antenna, and a charging coil electrically coupled to the battery, wherein the charging coil is positioned to receive electromagnetic energy and direct electrical current to charge the battery, and wherein the communication antenna is positioned to receive external control signals;
a controller positioned within the can and configured to direct electrical signals to the output terminal; and
a plurality of wires positioned to extend through the feed-throughs and operably couple the controller to the communication antenna and the battery to the charging coil.

10. A method for forming an implantable signal generator, the method comprising:
forming a shell;
positioning a battery and a controller within the shell;
forming a lid having a plurality of feed-throughs;
attaching the lid to the shell;
forming a charging coil and electrically coupling the charging coil to the battery;
forming a communication antenna and electrically coupling the communication antenna to the controller; and
positioning the communication antenna and the charging coil to be supported by the lid, external to the shell, wherein the communication antenna is positioned to receive external control signals, and wherein the charging coil is positioned to receive electromagnetic energy and direct electrical current to charge the battery.

11. The method of claim 10, further comprising: forming a header cap to encase the charging coil and the communication antenna.

12. The method of claim 10, wherein forming the charging coil includes forming a plurality of wire loops, and wherein the method further comprises positioning a first wire loop in a first plane and positioning a second wire loop in a second plane, the first plane is disposed at a non-zero angle relative to the second plane.

13. The method of claim 10, further comprising: forming a support element, wherein positioning the communication antenna and the charging coil to be supported by the lid includes attaching the communication antenna and the charging coil to the support element.

14. The method of claim 10, further comprising: forming a header cap having a curved surface.

\* \* \* \* \*

UNITED STATES PATENT AND TRADEMARK OFFICE
CERTIFICATE OF CORRECTION

PATENT NO. : 8,929,986 B2  
APPLICATION NO. : 13/669350  
DATED : January 6, 2015  
INVENTOR(S) : Jon Parker et al.

It is certified that error appears in the above-identified patent and that said Letters Patent is hereby corrected as shown below:

In the Specification

In column 9, line 11, delete "80d" and insert -- 802d --, therefor.

Signed and Sealed this
Fifth Day of May, 2015

Michelle K. Lee
*Director of the United States Patent and Trademark Office*